United States Patent [19]

Groppenbächer et al.

[11] 4,060,598
[45] Nov. 29, 1977

[54] TABLETS COATED WITH AQUEOUS RESIN DISPERSIONS

[75] Inventors: Gregor Groppenbächer, Mannheim-Feudenheim; Peter Rieckmann, Mannheim-Waldhof; Werner Rothe, Hockenheim, all of Germany

[73] Assignee: Boehringer Mannheim G.m.b.H., Mannheim, Germany

[21] Appl. No.: 626,513

[22] Filed: Oct. 28, 1975

Related U.S. Application Data

[60] Division of Ser. No. 463,216, April 22, 1974, Pat. No. 3,935,326, which is a continuation-in-part of Ser. No. 44,557, June 8, 1970, abandoned, which is a division of Ser. No. 740,058, June 26, 1968, abandoned.

[30] Foreign Application Priority Data

June 28, 1967 Germany ............................. 1617351

[51] Int. Cl.² .............................................. A61K 9/32
[52] U.S. Cl. ........................................ 424/33; 424/32
[58] Field of Search ......................... 424/20, 22, 33, 32

[56] References Cited

U.S. PATENT DOCUMENTS

| | | | |
|---|---|---|---|
| 3,275,518 | 9/1966 | Endicott et al. | 424/33 |
| 3,420,931 | 1/1969 | Daum et al. | 424/33 |
| 3,538,214 | 11/1970 | Polli et al. | 424/19 |

FOREIGN PATENT DOCUMENTS

268,497  7/1963  Australia.

*Primary Examiner*—Dolph H. Torrence
*Attorney, Agent, or Firm*—Burgess, Dinklage & Sprung

[57] ABSTRACT

Coated tablets are prepared by applying to a core of active material, at least one layer of a coating composition made up of a film forming aqueous synthetic resin dispersion and from 2–50% by weight of a water or alkaline soluble material and thereafter permitting the coating composition layer to dry. The resulting coated tablet has a core surrounded by a continuous porous matrix of synthetic resin formed from the aqueous dispersion which is insoluble in water and insoluble in the gastrointestinal tract. The pores of the continuous resin matrix are filled with a discontinuous particulate material which is water or alkaline soluble. The coated tablet initially is air and moisture tight.

19 Claims, 3 Drawing Figures

TABLETS COATED WITH AQUEOUS RESIN DISPERSIONS

RELATED APPLICATIONS

This is a division of application Ser. No. 463,216, filed Apr. 22, 1974, now U.S. Pat. No. 3,935,326 which is in turn a Continuation-in-Part of application Ser. No. 44,557, filed June 8, 1970, now abandoned, which is in turn a division of application Ser. No. 740,058 filed June 26, 1968, now abandoned.

BACKGROUND

This invention relates to coating compositions for tablets. More particularly this invention relates to tablet coating compositions which can be applied in thin layers, are impervious to heat and which result, as desired, in tablet coatings which are either water soluble or are only soluble in the small intestine.

In addition to the sugar coatings for dragees, which have been known for many years, recently several synthetic resin coating agents for tablets have been developed which in comparison with dragees, have the advantage that a satisfactory coating for tablets can be obtained with substantially less and thinner layers. Depending on the nature of the synthetic resins used, there are obtained coatings which are either water soluble or are resistant to gastric juices (cf. German Pat. Nos. 1,056,786 and 1,228,757).

A disadvantage of these synthetic resin coatings is that they have to be applied to the tablet cores in the form of their solutions in organic solvents, such as, for example, acetone, alcohol, chloroform, carbon tetrachloride and the like. Although these solvents evaporate very readily and, therefore, the finished coatings are obtained in a comparatively short period of time, these coating agents possess many significant disadvantages. These disadvantages include the following:

1. Large amounts of solvents are needed as the solids content in these coating agents usually cannot be much more than 20% due to the viscosity requirements;
2. The solvents, which are expensive in comparison with water, are either completely lost or can only be recovered by the use of very expensive apparatus;
3. Because of the toxicity of the solvent vapors, special safety measures must be provided in the working areas in order to protect personnel;
4. Most organic solvents are inflammable and mixtures of solvent vapors with air are explosive so that it is necessary to use expensive apparatus which is secure against possible fire and explosion.

In German Pat. No. 1,229,678, it has been proposed to apply molten polyethylene glycol to pre-heated tablet cores. This process admittedly avoids the use of solvents but then it necessitates the preparation of hot melts. Temperatures of up to 130° C are unusually high for use in the production of tablet coatings. All tubes, spray nozzles and the like of the involved apparatus, must be heatable in order to avoid a solidification of the polyethylene glycol inside of or on the surfaces of the apparatus.

Furthermore, the tablets have to be pre-heated which is something to be avoided, if possible, particularly in the case of heat sensitive active materials. A further disadvantage of this process is the fact that it can only be carried out with the use of the polyethylene glycols which, as are known, have a particularly unpleasant taste.

It is accordingly an object of the invention to provide a new field of tablet coating composition which can be applied in thin layers, are impervious to heat and which as desired, can either be water soluble or only soluble in the medium found in the small intestine.

It is another object of the invention to provide a method of producing tablet coating compositions of the character indicated.

A further object of the invention is to provide synthetic resin tablet coatings which do not require the use of organic solvents in either their preparation or deposition.

Still another object is to provide synthetic resin tablet coatings compositions which can be applied at room temperature and in fairly high concentrations, i.e., coating compositions which can be easily and simply applied to tablet cores.

Other objects and various features of novelty and invention will be pointed out or will occur to those skilled in the art from a reading of the following specification.

SUMMARY

The present invention provides a process for preparing coated tablets which comprises applying to a core of active material at least one layer of a coating composition comprising a film forming aqueous synthetic resin dispersion and from 2–50% by weight of a water or alkaline soluble material and thereafter permitting the coating composition layer to dry.

The coated tablet produced by the process of the invention can be characterized as including a core of active material which is soluble in the gastrointestinal tract and surrounded by a continuous porous matrix of synthetic resin formed from the film forming aqueous synthetic resin dispersion. The continuous resin matrix is insoluble in water and is thus insoluble in the gastrointestinal tract. The pores of the matrix contain from 15 to 600 %, based on the weight of the dried resin (film) matrix, a discontinuous or particulate material which is water or alkaline soluble. The coated tablet is initially air and moisture tight, but upon exposure to water or aqueous alkaline, the discontinuous soluble material in the continuous resin matrix will be dissolved from the pores thereof. Depending on the nature of the soluble, discontinuous material, the continuous resin matrix will remain intact becoming sufficiently porous thereby allowing the core of active material to diffuse out through the porous resin matrix, or will be torn apart, in the gastrointestinal tract.

DESCRIPTION OF THE DRAWING

The present invention will be more fully understood from the following description taken in conjunction with the accompanying drawing wherein.

DESCRIPTION

Figure 1:
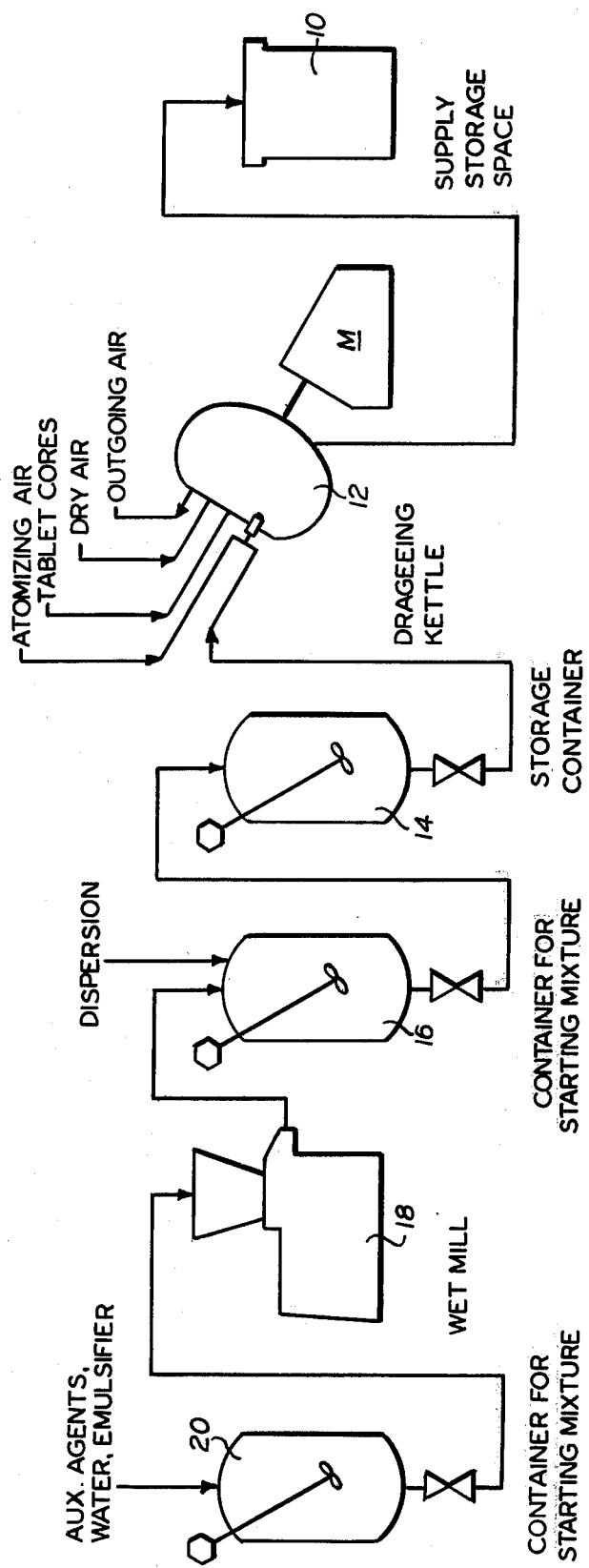
FIG. 1 is a schematic flow diagram with appropriate legends illustrating a preferred procedure for carrying out the process of the invention.

Film-forming aqueous synthetic resin dispersions are known from the paint technology field and are, in general, applied to a stationary substrate, movement or touching of the coated surface having to be carefully avoided until the drying is complete. Consequently, it was to have been expected that upon application of such synthetic resin dispersions to tablet cores moving about in a drageeing kettle, smooth surfaces would not be obtained but rather non-uniform, cracked coatings which would either stick to the walls of the kettle or would result in the tablet cores clumping together. These unsatisfactory results were to have been expected, particularly since the rubbing together of the tablet surfaces and the increasing concentration of the dispersions upon drying would give rise to the fear of premature coagulation and breakdown of the dispersion. In point of fact, the commercially available aqueous synthetic resin dispersions only result in the production of coherent, smooth surfaces when they additionally contain certain amounts of fillers.

According to the present invention, it is necessary to add materials which are water soluble or are soluble in alkaline solutions, which materials can be dissolved either by the gastric juices or by the alkaline juices in the small intestine, so that from the synthetic resin films which are initially completely air and moisture tight and are, therefore, also stable under tropical conditions, there are formed coatings which are permeable to the active materials present in the tablet cores. These materials which are water soluble or are soluble in alkaline solutions thereby simultaneously also act as the fillers which are necessary for process technical reasons. However, if desired, other insoluble fillers can additionally be added. The amount of these additives does not have to be very great. Thus, in accordance with the invention, it has been found that the use of the additives in an amount in toto of 5–6% is sufficient in order to make the synthetic resin dispersions suitable for tablet coatings.

Depending upon the requirements necessary for the particular coatings involved, there are used up to 50% of insoluble fillers and 2–50% of the materials which are water soluble or soluble in alkaline solutions, in both cases referred to the amount of aqueous synthetic resin dispersion used. With increasing amounts of the substances which are water soluble or soluble in alkaline solutions, the tablet coatings are more quickly and intensively attached in the stomach or small intestine and thus give rise to a coating which is sufficiently porous to allow the active materials present in the tablet cores to diffuse out through the coating.

When strongly swelling substances, so-called "disintegrating agents" are added in large amounts to the tablet cores, then it can easily happen that the porous coating is actually torn apart in the gastrointestinal tract. In this manner, the site and time of the liberation of the active material can be varied as desired depending upon the nature and amount of the additives employed. It is, in any case, possible to achieve breakdown and liberation times which are just as short as, or even shorter than, those of the best known dragees. However, according to the present invention, it is also possible to produce tablets having a considerably delayed liberation time or with an exclusively enteric liberation so that the new tablet coatings have a very wide field of application.

Further advantages of the new coating compositions according to the present invention and involving the use of aqueous dispersions of synthetic resins, are the avoidance of the use of organic solvents, the ability to work at ambient temperature and the relatively high proportion of solids. Thus, in contradistinction to solutions, the resultant viscosity of the aqueous synthetic resin dispersions permit a satisfactory working even in the case of concentrations of between 30 and 60%. As a result, it is possible to considerably shorten the drying times necessary for the removal of the water, which drying times are longer and require the use of more heat where organic solvents have been employed.

The application of the additive-containing aqueous synthetic resin dispersions according to the present invention can be carried out not only manually, as by pouring the coating compositions onto the tablet cores but also by spraying the same onto the cores using for the spraying semiautomatic or fully automatic devices. The application of the new coating compositions according to the present invention can be carried out in a particularly easy and simple fashion by means of the automatic drageeing apparatus described in German Pat. No. 1,247,547, which apparatus is manufactured under the mark "ZDS" by Strunck & Co., Cologne, Germany. When this apparatus is used, it is advantageous to wait for a short period of time after application of the coating composition to the moving tablet cores, i.e., until the applied amount of coating composition has been uniformly distributed over the cores before proceeding with the drying. Thereafter, drying is carried out with warm air or, preferably, with air at normal, i.e., room temperature until the cores no longer stick together, but roll smoothly over one another. Depending upon the shape and size of the tablet cores, as well as upon the composition of the coating agent, 5 to 10 coatings are usually sufficient to provide coatings upon the tablet cores which satisfy all requirements.

Surprisingly, with the use of the new coating compositions according to the present invention, it is possible for the first time, to apply, distribute and dry the coating compositions so that it is now no longer necessary, as was previously the case, to apply several layers in succession onto the tablets. On the contrary, a single, homogeneous coating results from a continuous application of the coating composition.

As aqueous synthetic resin dispersions for the coating compositions according to the present invention, there can, in principle, be used all pharmacologically compatible, film forming aqueous dispersions. Thus, for example, there can be used the commercially available dispersions of polyvinyl esters, polyvinyl acetals, polyvinyl chloride, butadienestyrene copolymers, polyacrylic acid esters and the like.

Aqueous synthetic resin dispersions used in the present invention are durable, milky dispersions of solid particles of synthetic resins having an average particle size in diameter of from 0.2–3 microns. The aqueous dispersions are similar to natural rubber latex and can be diluted, if desired, with water. The dispersions themselves are produced using known emulsion polymerization techniques.

The continuous porous resin matrix produced according to the present invention is formed by evaporating the water from the dispersion coating. The continuous resin matrix produced is generally clear, having the characteristics of a soft or flexible thermoplastic film. The continuous resin matrix are generally soluble in solvents, such as ketones, esters and aromatic and chlorinated hydrocarbons, but are completely insoluble in water. The continuous resin matrix is also generally regarded as being chemically resistant.

The properties of the tablet coatings produced according to the invention from aqueous synthetic resin dispersions are controlled by the addition of water and/or alkaline soluble materials to the aqueous dispersion, the amount of these soluble materials employed in the continuous resin coating (also used in conjunction with other inert materials as described above) are controlled so as to produce a tablet with a coating which will become permeable or porous or which will decompose in the gastrointestinal tract. Relatively small additions of soluble materials, for example up to about 50% by weight based on the weight of the dried resin matrix results in a slightly permeable tablet coating which is desired in the case of so-called retard preparations. Coatings designed to de-compose more readily, for example in the digestive juices present in the stomach require a larger amount of soluble materials, for example up to 600% by weight based on the weight of the dried resin matrix. Coatings for retard preparations which are resistant to gastric juices employ either an alkaline soluble material in the continuous resin matrix and/or the incorporation of carboxyl groups into the resin matrix via the aqueous dispersion itself.

Prior to the present invention, tablet coating with synthetic resin films was carried out using organic solvent coating techniques. Water has been used but only to carry out auxiliary functions in conjunction with organic solvent coating procedures (cf. Australian Pat. No. 268,497). Prior to the present invention, tablet coating with synthetic resins based solely on an aqueous coating technique was not possible. Prior attempts using water soluble film forming resins, such as cellulose derivatives and polyvinyl alcohol were not successful because the aqueous coating solution could only contain low concentrations of the soluble resin. This resulted in an undesirable water attack on the surface of the core of active material itself to say nothing of the complicated coating and drying techniques themselves.

Contrary to what the art would have expected, the present invention makes it possible to coat tablets with synthetic resins using a totally aqueous system. This is possible because the aqueous resin dispersions can be used in a highly concentrated form, which means that a substantially smaller amount of water has to be evaporated to form a dried, finished coating. The present invention also employs quick drying of the coated tablets, such as by the dipping tube method, which results in a rapid evaporation of the water which effectively prevents the water from reaching and penetrating into the core of active material. Moreover, because the aqueous resin dispersions form a durable synthetic resin film, soluble auxiliary material, such as described herein can be incorporated into the film or a continuous resin matrix in a controlled manner.

Thus, it was not believed possible to use a totally aqueous coating technique for producing coated tablets and it was also thought that under high mechanical stresses as occur in a tablet coating process that the colloidal resin particles would undergo a premature coagulation resulting in a non-uniform and non-coherent coating on the tablet core, especially in the presence of auxiliary materials, such as the water or alkaline soluble materials and filling agents (cf. Hans Reinhard: "*Dispersionen Synthetischer Hochpolymerer*", part II application, pages 8-10). The coating process of the invention also provides processing advantages from an environmental standpoint. Prior to the present invention, the use of organic solvents required elaborate procedures and techniques to protect the worker and his environment as well as to prevent the expulsion of unwanted solvent vapors into the atmosphere. Because the present invention is based totally on an aqueous dispersion coating technique, all of these problems are avoided thereby enhancing the economics and the environmental compatibility of the claimed process.

Suitable dispersions are:

a. Mowilith DM 1, manufactured by Hoechst consisting of a 50% aqueous dispersion of a mixed polymerisate of vinylacetate and maleic acid ester, characterized by a particle size of 0.3–2 $\mu$, a pH of 4–5, a resistance to cold down to $-18°$ C and comprising polyvinylalcohol as protective-colloid. The viscosity of the dispersion was determined at ambient temperature (20° C) by means of a "Ford-viscosimeter"; nozzle: 6mm; time of outflow: 10 seconds.

b. Mowilith DM 20, manufactured by Hoechst consisting of a 50% aqueous dispersion of a mixed polymerisate comprising vinylacetate, characterized by a particle size of 0.2–3 $\mu$ and a pH of 4–5. The viscosity of the dispersion was determined at ambient temperature by means of a "Ford-viscosimeter"; nozzle: 6mm; time of outflow: 10 seconds.

c. Propiofan 590 D, manufactured by BASF consisting of a 50% aqueous dispersion of a mixed polymerisate comprising vinylpropionate and a non-ionogenic emulsifier, characterized by a pH of 5 to 7 and a particle size of 0.2–3 $\mu$. The viscosity of the dispersion was determined at a temperature of 20° C by means of a "Ford-viscosimeter"; nozzle: 6mm; time of outflow: 45 seconds.

d. Lutofan 300D, manufactured by BASF consisting of a 50% aqueous dispersion of a mixed polymerisate comprising vinylchloride and a non-ionogenic emulsifier characterized by a pH of about 5 and a particle size of about 1 $\mu$. The viscosity of the dispersion was determined at a temperature of 20° C by means of a "Ford-viscosimeter"; nozzle: 6mm; time of outflow: 5 seconds.

e. Acronal 14D, manufactured by BASF consisting of a 50% aqueous dispersion of a mixed polymerisate of acrylic-esters and a non-ionogenic emulsifier, characterized by a pH of 5–7 and a particle size of about 0.3 $\mu$. The viscosity of the dispersion was determined at a temperature of 20° C by means of a "Ford-viscosimeter"; nozzle: 6mm, time of outflow: 5 seconds.

f. Litex SB 40, manufactured by Chemische Werke Huls consisting of a 50% aqueous dispersion of a mixed polymerisate of 60% styrene, 40% butadiene and a non-ionogenic emulsifier, characterized by a pH of 9–10 and a particle size of about 0.2 $\mu$. The viscosity of the dispersion was determined at a temperature of 20° C by means of a "Ford-visosimeter"; nozzle: 6mm; time of outflow 5 seconds.

Preferred aqueous synthetic resin dispersions in the process of the invention are dispersions based on polyacrylates. These materials are preferred because of their physiological compatibility and desirable toxicological properties. In addition to ACRONAL 14D described above, commercially available polyacrylates can be used. For example EUDRAGIT L 30D and EUDRAGIT E 30D, manufactured by Röhm Pharma GmbH., Darmstadt, Germany, can be used as aqueous polymer dispersions for manufacturing rapidly disintergrating film tablets and delayed-release preparations according to the present invention. These two aqueous polymer dispersions are plasticizer-free, acrylic resin dispersions containing 30% solids which form a clear, flexible film built-up from poly(meth)acrylic acid esters. Both films formed from these polymer dispersions are insoluble in water which is a common characteristic to all aqueous synthetic resin dispersions used in the present invention.

Illustrative of the fillers which, for process technical reasons, are to be added to the dispersions, are talc, chalk, kaolin, maize starch, rice starch, highly dispersed silicic acid and the like.

As examples of water-soluble materials suitable for incorporation into the coating compositions, there may be mentioned salts, sugars, polyethylene glycols, polyvinyl pyrrolidones, wherein the polyethylene glycols can simultaneously act as lubricants and the polyvinyl pyrrolidones can simultaneously act as adhesives. Another water soluble adhesive which can, if desired, be added is starch syrup.

Typical examples of water soluble substances for this purpose are sodium chloride, saccharose, lactose, glucose, sorbitol mannitol, polyethylenglycol 20,000, polyvinylpyrrolidone ("Kollidon 25" from BASF) and polyvinylalcohol ("Mowiol N 30–98" from Hoechst).

As illustrative of the alkali-soluble materials for inclusion with coating compositions and which are resistant to gastric juices, there can be mentioned all physiologically compatible acidic solid materials, such as the higher fatty acids, as for example lauric acid, palmitic acid, stearic acid, polyacrylic acid and polymethacrylic acid.

Further additives which, if desired, can be added to the synthetic resin dispersions include dyestuffs, colored pigments, flavorings and preserving agents.

If the final film is to be particularly soft and elastic, then plasticizers, such a phthalic acid esters, can be also added, preferably in the form of their emulsions.

For the production of the final mixture, it is advantageous to first stir up the powdered solid materials with demineralized water, as well as possibly with small amounts of an emulsifying agent and/or a wetting agent in order to provide a suspension, the viscosity of which is similar to that of the synthetic resin dispersion, and then slowly to mix it with the latter. After a thorough homogenization of the resultant mixture, the composition can be used immediately.

In some cases, it has proved to be advantageous to apply a layer of pure polyvinyl alcohol, polyvinyl pyrrolidone or solid polyethylene glycol to the tablet cores before the application of the first layer of the coating composition of the invention. Furthermore, it is, of course, also possible to first apply a coating which is resistant to gastric juices, followed by the application of further layers of the coating composition according to the present invention. In this manner, there are obtained tablets from which the active materials are belatedly liberated in the small intestine and then by slow diffusion.

The finished tablet cores coated with the composition according to the present invention, are generally only 5–15% heavier than the original cores because completely unbroken coatings are obtained when the amount of composition is applied is only about 3% of the weight of the tablet core. Furthermore, a subsequent polishing or waxing, as in the case of dragees, is completely unnecessary because the finished synthetic resin coatings have themselves a permanent, silky gloss.

The tablet or pill cores which are coated with the compositions of the invention can be pharmaceutical in nature, confectionary materials or gum centers.

The following Examples are given for the purpose of illustrating the present invention but in no way are to be construed as a limitation thereof.

Referring now to the drawing and in particular FIG. 1, apparatus for carrying out the process of the invention in a preferred manner is shown to include a storage container 20 from which auxiliary agents such as the water or alkaline soluble materials and inert fillers are fed to the wet mill 18. The auxiliary agents from wet mill 18 are combined with synthetic aqueous resin dispersion in container 16 and then fed to storage container 14. From the container 14 the aqueous resin dispersion is atomized into tablet coating kettle 12 which is set to rotate at an angle so as to effectively tumble the contents thereof. Tablet cores to be coated are introduced through the cover of the kettle 12 along with dry air. The dry air, after contacting the wet, coated cores absorbs water and exits from the line indicated in the cover of the kettle 12. Coated, dried, finished tablets then move from the kettle 12 to the storage container 10 from where they can be packaged or otherwise dispensed.

The coating and drying procedure carried out in kettle 12 represents a preferred manner for carrying out the process of the invention. Thus, in kettle 12, tablet cores to be coated are introduced into a rotating, angled tumbling zone. At the same time, aqueous synthetic resin dispersion is atomized or sprayed into the tumbling zone so as to uniformly and rapidly contact and coat the tablet cores. At the same time dry air is injected into the tumbling zone. Because of the motion of the zone causing the coated tablets to continually tumble, the dry air thoroughly and quickly contacts the wet coated cores and by this action rapidly and efficiently removes the water medium resulting in a dried, uniform coating on the tablet cores. Water saturated air is continually withdrawn from the tumbling zone 12 to enhance the coating and drying operation. Thus, by carrying out the coating and drying operation as described, using an aqueous dispersion of resin containing from 30–60% polymer solids it is possible to efficiently coat tablet cores without having the water medium from the aqueous dispersion adversely affect the cores themselves. Instead, rapid drying in tumbling zone 12 via atomized resin dispersion and the injection of dry air results in a uniformly coated tablet of high quality.

Figure 2A:
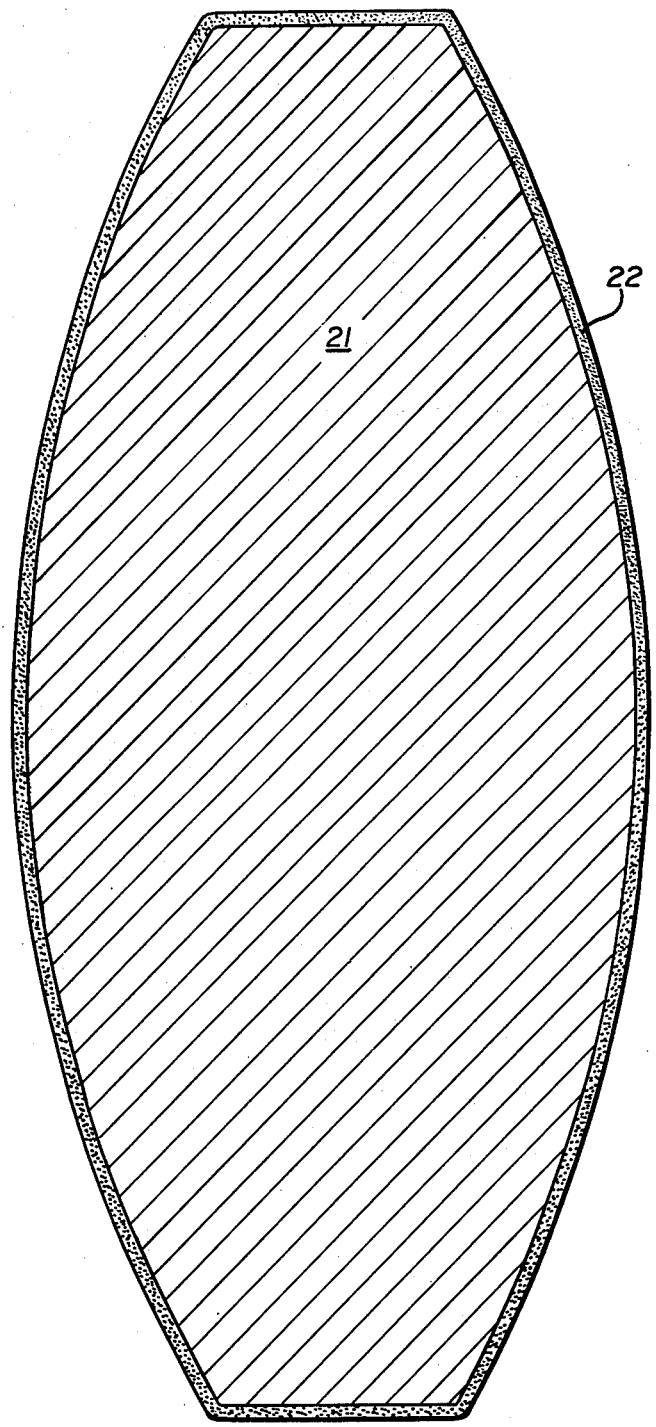
FIG. 2a is an enlarged cross-sectional view of a tablet coated according to the present invention.

FIG. 2a is a representation in cross-section of a coated tablet prepared according to the present invention. The core of active material is identified by reference numeral 21 and the tablet coating applied via the process of the invention is identified by the reference numeral 22.

Figure 2B:
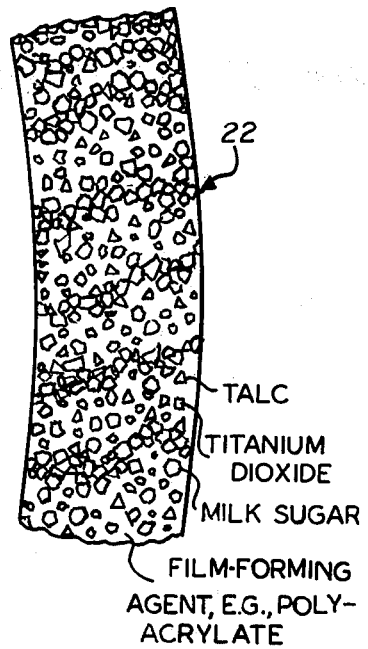
FIG. 2b is an enlarged microscopic view of a tablet coating formed according to the present invention.

In FIG. 2b there is shown a microscopic view of a preferred coating formed according to the process of the invention. The coating is shown to include a continuous porous matrix of polyacrylate formed from a film forming aqueous synthetic dispersion of polyacrylate. The continuous matrix is filled with auxiliary agents which in this illustration include talc, tatanium dioxide and milk sugar.

EXAMPLE 1

13 Parts of talc, 1 part of polyethylene glycol (average molecular weight 20,000) and 1 part of tartrazin (foodstuff yellow No. 2, EWG No. E 102) were suspended in 70 parts of demineralized water and, under continuous stirring, mixed with 200 parts of an approximately 50% aqueous polyvinyl acetate dispersion ("Mowilith DM1"). The solids content of the resulting coating agent amounted to 40.3%.

There was manually applied a quantity of this mixture onto placebo cores rotating in a conventional drageeing kettle so that all of the cores were moistened. After waiting until the applied liquid had been uniformly distributed on the moving cores, they were then dried by blowing on of air. As soon as the first layer was dry, which state can easily be recognized as the cores roll smoothly over one another, the next layer was applied in the same manner. Following the application of eight layers, there was obtained a completely unbroken lacquer coating which had a silky gloss, and which required no further treatment. The tablet cores thereby increased in weight by an average amount of about 10%.

EXAMPLE 2

Six parts of talc, 6 parts of saccharose, 3 parts of polyethylene glycol (average molecular weight 20,00) and 1 part of tartrazin were suspended in 90 parts of demineralized water and mixed, under continuous stirring, with 200 parts of an approximately 50% aqueous polyvinyl acetate dispersion ("Mowilith DM 1"). The solids content of the mixture amounted to 38.2%.

On to placebo cores rotating in a conventional drageeing kettle, there was applied, using for the spraying a ZDS automatic spraying apparatus according to German Pat. No. 1,247,547, several layers of this mixture in such a manner that six layers resulted in a weight increase of the cores of 4–5%. The uniform cores thus obtained, which had a silky gloss, had breakdown times which were as good as those of dragees.

Similar results were obtained with the use of a mixture of 200 parts of polyvinyl acetate dispersion ("Mowilith DM 1") and a suspension which contained 25 parts of talc, 5 parts of polyethylene glycol (average molecular weight 20,000) and 3 parts polyvinyl alcohol ("Mowiol N 30-98") in 100 parts of demineralized water.

EXAMPLE 3

Ten parts of saccharose, 5 parts of polyethylene glycol (average molecular weight 4,000) and 1 part of Ponceau 6R (foodstuff red No. 1, EWG No. E 126) were dissolved in 125 parts of demineralized water and then mixed with 200 parts of polyvinyl acetate dispersion ("Mowilith DM 1").

This dispersion was sprayed continuously onto placebo cores rotating in a conventional drageeing kettle in an amount which corresponded to about 30% of the weight of the cores. Simultaneously, vigorous drying with air was carried out. In this method of working, it was only necessary to take care that the drying was not too weak. Apart from the waste of energy, too strong a drying is not harmful. In this manner, there were obtained tablets with a single homogeneous coating which constituted about 10% of the weight of the cores. The breakdown times thereof corresponded to those of good dragees.

EXAMPLE 4

Suspensions of the compositions set out in the following Table I were each mixed with 200 parts of an aqueous approximately 50% polyvinyl acetate dispersion ("Mowilith DM 20").

TABLE I

| FORMULATION NO. | 1 | 2 | 3 | 4 | 5 |
|---|---|---|---|---|---|
| talc | 13 | 10 | | | |
| chalk | | | 40 | | |
| rice starch | | | | 50 | 100 |
| highly-dispersed silicic acid ("Acrosil") | | | | 2.5 | 5 |
| saccharose | | | 5 | 10 | 10 |
| polyethylene glycol (average MW 20,000) | 10 | 10 | 15 | 5 | 20 |
| polyvinyl pyrrolidone ("Kollidon 25") | | | 4 | 3 | |
| starch syrup | | | 5 | | |
| polyvinyl alcohol ("Mowiol N 30-98") | 5 | | | | |
| emulsifying agent ("Cremophor EL") | | | | 0.5 | 0.5 |
| tartrazin | 2 | | | 1 | 1 |
| Ponceau 6R | | 1 | 1 | | |
| demineralized water | 150 | 75 | 100 | 130 | 180 |

The solids content of the final, mixed coating agents according to formulations 1 to 5 varied between 34 and 46%.

All of the above-described mixtures gave satisfactory coatings. In particular, formulations 4 and 5 gave coatings having exceptionally low breakdown times which were far superior to those of good dragees.

EXAMPLE 5

100 Parts of talc, 25 parts of polyethylene glycol (average molecular weight 20,000), 0.5 parts of sodium lauryl sulfate, 2 parts of titanium dioxide and 1 part of tartrazin were suspended in 170 parts of demineralized water and the suspension then mixed with 200 parts of an approximately 50% aqueous polyvinyl propionate dispersion ("Propiofan 590 D").

When this mixture was applied to tablet cores using the procedure described in Example 2, there were obtained tablet coatings characterized by their good appearance, and which were pharmacologically satisfactory.

Satisfactory results were also obtained by mixing 200 parts of the same synthetic resin dispersion with a suspension of 20 parts of polyethylene glycol (average molecular weight 4,000), 5 parts of ferric oxide pigment in 50 parts of demineralized water.

EXAMPLE 6

15 Parts of chalk, 8 parts of saccharose, 0.5 parts of sodium lauryl sulfate, 10 parts of titanium dioxide and 60 parts of demineralized water were mixed together and then the mixture intimately stirred up with 200 parts of an approximately 50% aqueous polyvinyl chloride dispersion ("Lutofan 300 D").

By further working according to the method described in Examples 1 and 2, there was obtained satisfactory tablet coatings.

EXAMPLE 7

20 Parts of maize starch, 5 parts of polyethylene glycol, 5 parts of polyvinyl alcohol ("Mowiol N 30-98"), 3 parts of titanium dioxide, 1 part of Ponceau 6R and 90 parts of demineralized water were, in suspended form, mixed with 200 parts of an approximately 50% aqueous dispersion of polyacrylic acid esters ("Acronal 14 D") and the resulting mixture then applied to tablet cores according to the method described in the preceding Examples. There were thusly obtained pharmacologically satisfactory, pink colored tablet coatings which had a good gloss.

Coatings with a different, deeper red color, as well as somewhat shorter breakdown times, were obtained by admixture of the same synthetic resin dispersion with an aqueous suspension of 25 parts of talc, 5 parts of saccharose, 5 parts of polyethylene glycol (average molecular weight 20,000), 5 parts of ferric oxide pigment and 2 parts of titanium dioxide in 80 parts of demineralized water.

EXAMPLE 8

Example 7 is duplicated using a place of ACRONAL 14 D, EUDRAGIT L 30D and EUDRAGIT E 30D aqueous polyacrylate dispersions. Good results are obtained.

EXAMPLE 9

20 Parts of talc, 30 parts of chalk, 7 parts of saccharose, 2 parts of polyvinyl pyrrolidone ("Kollidon 25"), 10 parts of ferric oxide pigment were suspended in 120 parts of demineralized water and mixed with 200 parts of an approximately 50% aqueous dispersion of a butadiene-styrene copolymer ("Litex SB 40").

When this mixture was applied to tablet cores by the method described in Examples 1 or 2, there were obtained pharmacologically satisfactory tablet coatings of good appearance which broke down about as quickly as good dragees.

What is claimed is:

1. Coated tablet comprising a core of active material soluble in the gastrointestinal tract and a coating surrounding said core said coating comprising a continuous porous matrix of a synthetic resin insoluble in the gastrointestinal tract and a water or alkaline soluble material in the pores of said matrix, said coating being formed by applying to said core at least one layer of a coating composition of a film forming aqueous zynthetic resin dispersion with a resin content between 30 and 60% by weight and from 2 to 50% by weight of said water or alkaline soluble material and permitting said coating composition layer to dry, said coated tablet being initially air and moisture tight.

2. Coated tablet of claim 1 wherein said water soluble material is selected from the group consisting of salt, sugar, polyethylene glycol, polyvinyl pyrrolidone and starch syrup.

3. Coated tablet of claim 1 wherein said alkaline soluble material is a higher fatty acid.

4. Coated tablet of claim 1 wherein said alkaline soluble material is lauric acid.

5. Coated tablet of claim 1 wherein said synthetic resin is a member selected from the group consisting of polyvinyl ester, polyvinyl acetal, polyvinyl chloride, butadiene-styrene copolymer and polyacrylic acid ester.

6. Coated tablet of claim 1 additionally containing an insoluble filler.

7. Coated tablet of claim 1 wherein said insoluble filler is present in an amount of up to 50% referred to the amount of aqueous synthetic resin dispersion.

8. Coated tablet of claim 6 wherein said insoluble filler is a member selected from the group consisting of talc, chalk, kaolin, maize starch, rich starch and highly dispersed silicic acid.

9. Coated tablet of claim 1 additionally containing at least one member selected from the group consisting of dye stuffs and colored pigments.

10. Coated tablet of claim 1 additionally containing at least one member selected from the group consisting of flavoring agents and perservatives.

11. Coated tablet of claim 1 additionally containing a plasticizer.

12. Coated tablet of claim 11 wherein said plasticizer is a phthalic acid ester.

13. Coated tablet of claim 1 wherein said coating comprises 200 parts of an approximately 50% aqueous polyvinyl acetate dispersion, 13 parts of talc, 1 part of polyethylene glycol (average molecular weight 20,000) 1 part of tartrazin and 70 parts demineralized water.

14. Coated tablet of claim 1 wherein said coating comprises 200 parts of an approximately 50% aqueous polyvinyl acetate dispersion, 6 parts of talc, 6 parts of saccharose, 3 parts polyethylene glycol (average molecular weight 20,000), 1 part of tartrazin and 90 parts demineralized water.

15. Coated tablet of claim 1 wherein said coating comprises 200 parts of an approximately 50% aqueous polyvinyl propionate dispersion, 100 parts talc, 25 parts polyethylene glycol (average molecular weight 20,000) 0.5 parts sodium lauryl sulfate, 2 parts of titanium dioxide, 1 part tartrazin and 170 parts demineralized water.

16. Coated tablet of claim 1 wherein said coating comprises 200 parts of an approximately 50% aqueous polyvinyl chloride dispersion, 15 parts chalk, 8 parts saccharose, 0.5 parts sodium lauryl sulfate, 10 parts titanium dioxide and 60 parts demineralized water.

17. Coated tablet of claim 1 wherein said coating comprises 200 parts of an approximately 50% aqueous dispersion of polyacrylic acid ester, 20 parts maize starch, 5 parts polyethylene glycol, 5 parts polyvinyl alcohol, 3 parts titanium dioxide, 1 part Ponceau-6R and 90 parts demineralized water.

18. Coated tablet of claim 1 wherein said coating comprises 200 parts of an approximately 50% aqueous dispersion of a butadiene-styrene copolymer, 20 parts talc, 30 parts chalk, 7 parts saccharose, 20 parts polyvinyl pyroolidone, 10 parts ferric oxide pigment and 120 parts demineralized water.

19. Coated tablet of claim 1 wherein said coating comprises a 30 to 50% aqueous, plasticizer-free acrylic resin dispersion.

* * * * *